United States Patent
Jaeschke et al.

(10) Patent No.: US 7,659,401 B2
(45) Date of Patent: Feb. 9, 2010

(54) THIAZOLO[4,5-C]PYRIDINE DERIVATIVES

(75) Inventors: Georg Jaeschke, Basel (CH); Sabine Kolczewski, Rheinfelden (DE); Richard H. P. Porter, Reinach BL (CH); Patrick Schnider, Bottmingen (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 266 days.

(21) Appl. No.: 11/590,087

(22) Filed: Oct. 31, 2006

(65) Prior Publication Data

US 2007/0105891 A1     May 10, 2007

(30) Foreign Application Priority Data

Nov. 8, 2005   (EP)  ................. 05110461

(51) Int. Cl.
   *C07D 513/02*     (2006.01)
   *C07D 401/00*     (2006.01)

(52) U.S. Cl. ....................... 546/114; 544/324
(58) Field of Classification Search ................. 546/114; 544/324
See application file for complete search history.

(56) References Cited

U.S. PATENT DOCUMENTS 6,660,753 B2    12/2003    Van Wagenen et al.

FOREIGN PATENT DOCUMENTS

| EP | 321115 | 6/1989 |
|----|--------|--------|
| EP | 1210344 | 6/2002 |
| WO | WO 98/05651 | 2/1998 |
| WO | WO 02/44189 | 6/2002 |
| WO | WO 02/068417 | 9/2002 |
| WO | WO 02/078745 | 10/2002 |
| WO | WO 2004/067002 A2 | 8/2004 |
| WO | PCT/GB2006/001242 * | 4/2005 |
| WO | WO 2006/008545 | 1/2006 |

OTHER PUBLICATIONS

Bonnefous et al., Bioorganic & Medicinal Chem. Letters, vol. 15, Issue 4 (Feb. 15, 2005) pp. 1197-1200.
Mutel, V., Expert Opin. Ther. Patents (2002) 12(12) pp. 1845-1852.
Suzuki et al., Synthesis, (1982) pp. 874-875.
Basha et al., Tetrahedron Lett. (1977) vol. 48, pp. 4171-4174.
Golankiewicz et al., Tetrahedron (1985) vol. 41, pp. 5989-5994.
Schlaeger et al., Cytotechnology vol. 30 pp. 71-83 (1999).
Porter et al., Br. J. Pharmacol. vol. 128, pp. 13-20 (1999).
Storto et al., European Journal of Pharmacology (2004) vol. 497(1) pp. 25-27.
Abriss, et al., Journal of Hepatology (2003) vol. 38, pp. 169-178.
Storto, et al., Hepatology (Philadelphia) (2000) vol. 31(3) pp. 649-655.
Vincent Mutel, Exp. Opin. Ther. Pat., vol. 12, pp. 1845-1852 (2002), XP002394958.
Varty, G. et al, *Psychopharmacology*, 179(1): 207-217 (2005).

* cited by examiner

*Primary Examiner*—Janet L. Andres
*Assistant Examiner*—Raymond Covington
(74) *Attorney, Agent, or Firm*—George W. Johnston; Patricia S. Rocha-Tramaloni; Kimberly J. Prior

(57) ABSTRACT

The invention relates to compounds of general formula I:

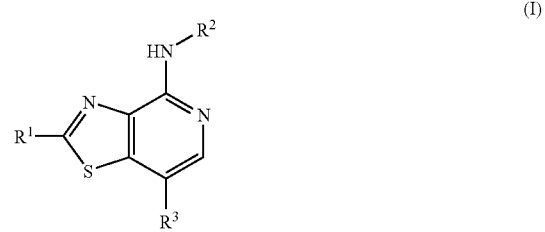

wherein $R^1$, $R^2$ and $R^3$ are as defined in the description such compounds are metabotropic glutamate receptor antagonists and are useful in the treatment or prevention of mGluR5 receptor mediated disorders.

24 Claims, No Drawings

THIAZOLO[4,5-C]PYRIDINE DERIVATIVES

PRIORITY TO RELATED APPLICATIONS

This application claims the benefit of European Application No. 05110461.0, filed Nov. 8, 2005, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR's are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia, gastrointestinal reflux disorder and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

SUMMARY OF THE INVENTION

The present invention provides heterocyclic derivatives of formula I

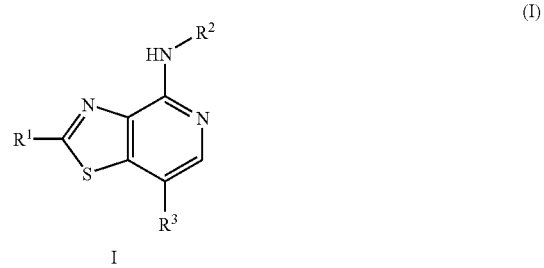

wherein
$R^1$ is hydrogen, halogen, cyano, lower alkoxy, lower alkyl, lower alkyl substituted by halogen, cycloalkyl, —(CH$_2$)$_n$—O-lower alkyl, or —C(O)R' wherein R' is lower alkyl, lower alkoxy or N(R)$_2$;
$R^2$ is aryl or 5-or 6-membered heteroaryl;
$R^3$ is hydrogen, OR, N(R)$_2$, lower alkyl, cycloalkyl, aryl, heterocycloalkyl, 5-or 6-membered heteroaryl, C(O)N(R)$_2$, lower alkyl substituted by halogen, or —C(O)R' wherein R' is lower alkyl, lower alkoxy or N(R)$_2$;
wherein the aryl, cycloalkyl, heterocycloalkyl or 5-or 6-membered heteroaryl groups for $R^2$ and $R^3$ are unsusbtituted or substituted by halogen, cyano, lower alkyl, lower alkoxy, S(O)$_2$-alkyl, S(O)-alkyl, or —C(O)R' wherein R' is lower alkyl, lower alkoxy or N(R)$_2$;
R is hydrogen or lower alkyl;
n is 0, 1 or 2;

and pharmaceutically acceptable salts thereof.

The invention also provides pharmaceutical compositions comprising a therapeutically effective amount of a compound of formula I and a pharmaceutically acceptable carrier. The invention further provides methods for preparing the compounds and compositions of the invention.

The compounds of formula I are metabotropic glutamate receptor antagonists. Compounds of formula I are distinguished by having valuable therapeutic properties. They can be used in the treatment or prevention of mGluR5 receptor mediated disorders.

Such disorders are acute and/or chronic neurological disorders, in particular acute or chronic pain, urinary incontinence, gastrointestinal reflux disorder, liver damage or failure whether drug or disease induced, obesity or Fragile-X or autism, acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression and drug dependency.

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

The term "lower alkyl" used in the present description denotes a straight-chain or branched saturated hydrocarbon residues having 1 to 6 carbon atoms, preferably 1 to 4 carbon atoms, such as methyl, ethyl, n-propyl, i-propyl, n-butyl, t-butyl and the like.

The term "lower alkoxy" denotes a lower alkyl residue in as defined above bound via an oxygen atom. Examples of "lower alkoxy" residues include methoxy, ethoxy, isopropoxy and the like.

The term "halogen" denotes fluorine, chlorine, bromine and iodine.

The term "lower alkyl substituted by halogen" denotes a lower alkyl group as defined above which is substituted by one or more halogen atom. Examples of such group include, but are not limited to, methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred groups are difluoro- or trifluoro-methyl or ethyl.

"Aryl" represents an aromatic carbocyclic group consisting of one individual ring or one or more fused rings in which at least one ring is aromatic in nature. Preferred aryl group is phenyl.

The term "5-or 6-membered heteroaryl" refers to an aromatic ring containing one or more heteroatoms selected from nitrogen, oxygen and sulphur. Preferred are those heteroaryl groups selected from nitrogen. Examples of such heteroaryl groups include pyridinyl, pyrazinyl, pyrazolyl, pyrimidinyl, pyridazinyl, isoxazolyl or thiazolyl.

The term "heterocycloalkyl" refers to a saturated non-aromatic ring containing one or more heteroatoms selected from nitrogen, oxygen and sulphur, the rest of the ring atoms being carbon atoms. Preferred heterocycloalkyl are heterocycloalkyl having 5 or 6 ring members. Preferred are those heterocycloalkyl groups selected from nitrogen. Examples of such groups include morpholinyl, tetrahydropyranyl, thiomorpholinyl, piperazinyl, pyrrolidinyl or piperidyl.

The term "cycloalkyl" denotes a saturated carbocyclic group, containing 3-12 carbon atoms, preferably 3-6 carbon atoms.

The aryl, 5- or 6-membered heteroaryl, heterocycloalkyl, and cycloalkyl groups are unsubstituted or substituted by one or more substituents. Examples of such substituents include halogen, lower alkyl, and $SO_2$-lower alkyl, as well as those groups depicted in the specific examples appended hereto.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to any salt derived from an inorganic or organic acid or base. Such salts include acid addition salts formed with inorganic acids such as hydrochloric acid, hydrobromic acid, sulfuric acid, nitric acid, phosphoric acid; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid or trimethylacetic acid.

"Therapeutically effective amount" means an amount that is effective to prevent, alleviate or ameliorate symptoms of disease or prolong the survival of the subject being treated.

The present invention provides heterocyclic derivatives of formula I

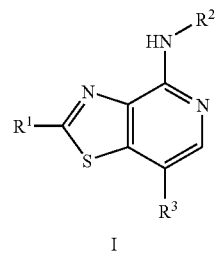

wherein
$R^1$ is hydrogen, halogen, cyano, lower alkoxy, lower alkyl, lower alkyl substituted by halogen, cycloalkyl, —(CH$_2$)$_n$—O-lower alkyl, or —C(O)R' wherein R' is lower alkyl, lower alkoxy or N(R)$_2$;
$R^2$ is aryl or 5-or 6-membered heteroaryl;
$R^3$ is hydrogen, OR, N(R)$_2$, lower alkyl, cycloalkyl, aryl, heterocycloalkyl, 5-or 6-membered heteroaryl, C(O)N(R)$_2$, lower alkyl substituted by halogen, or —C(O)R' wherein R' is lower alkyl, lower alkoxy or N(R)$_2$;
wherein the aryl, cycloalkyl, heterocycloalkyl or 5-or 6-membered heteroaryl groups for $R^2$ and $R^3$ are unsubstituted or substituted by halogen, cyano, lower alkyl, lower alkoxy, S(O)$_2$-alkyl, S(O)-alkyl, or —C(O)R' wherein R' is lower alkyl, lower alkoxy or N(R)$_2$;
R is hydrogen or lower alkyl;
n is 0, 1 or 2;

and pharmaceutically acceptable salts thereof.

Preferred are compounds of formula I,

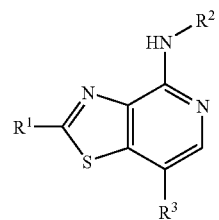

wherein
$R^1$ is lower alkyl;
$R^2$ is phenyl, thiazolyl, pyridinyl, pyrimidinyl or pyrazolyl, wherein the rings are unsubstituted or substituted by halogen or lower alkyl;
$R^3$ is hydrogen, phenyl, pyridinyl, pyrimidinyl or isoxazolyl which are each unsubstituted or substituted by halo or —SO$_2$-lower alkyl;

and pharmaceutically acceptable salts thereof.

Preferred are compounds of formula I,

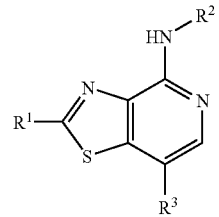

wherein
R¹ is lower alkyl;
R² is phenyl, thiazolyl, pyridinyl or pyrazolyl, wherein the rings are unsubstituted or substituted by halogen or lower alkyl;
R³ is hydrogen or pyridinyl;

and pharmaceutically acceptable salts thereof.

Most preferred are compounds of formula I, wherein R¹ is methyl.

Preferred compounds of formula I are further those, wherein R³ is hydrogen and R² is phenyl substituted by halogen, for example the following compound (3-chloro-phenyl)-(2-methyl-thiazolo[4,5-c]pyridin-4-yl)-amine.

Other preferred compounds are those wherein R³ is pyridine-3-yl.

Among these compounds are compounds of formula I, wherein R³ is pyridin-3-yl and R² is methyl-substituted thiazolyl, for example the following compounds:
(2-methyl-7-pyridin-3-yl-thiazolo[4,5-c]pyridin-4-yl)-(2-methyl-thiazol-4-yl)-amine and
(2-methyl-7-pyridin-3-yl-thiazolo[4,5-c]pyridin-4-yl)-(4-methyl-thiazol-2-yl)-amine.

Preferred compounds of formula I are further those, wherein R³ is pyridin-3-yl and R² is halogen-substituted pyridinyl, for example the following compound:
(5-fluoro-pyridin-2-yl)-(2-methyl-7-pyridin-3-yl-thiazolo[4,5-c]pyridin-4-yl)-amine.

Preferred compounds of formula I are further those, wherein R³ is pyridin-3-yl and R² is methyl substituted pyrazol-3-yl, for example the following compound:
methyl-1H-pyrazol-3-yl)-(2-methyl-7-pyridin-3-yl-thiazolo[4,5-c]pyridin-4-yl)-amine.

Preferred compounds of formula I are further those, wherein R³ is pyridin-3-yl substituted by halogen or lower alkyl and R² is methyl-substituted thiazolyl, methyl-substituted pyridinyl or methyl-substituted pyrimidinyl, for example the following compounds:
[7-(5-Fluoro-pyridin-3-yl)-2-methyl-thiazolo[4,5-c]pyridin-4-yl]-(4-methyl-thiazol-2-yl)-amine;
[7-(5-Fluoro-pyridin-3-yl)-2-methyl-thiazolo[4,5-c]pyridin-4-yl]-(2-methyl-pyrimidin-4-yl)-amine;
[7-(5-Fluoro-pyridin-3-yl)-2-methyl-thiazolo[4,5-c]pyridin-4-yl]-(2-methyl-thiazol-4-yl)-amine;
[7-(5-Fluoro-pyridin-3-yl)-2-methyl-thiazolo[4,5-c]pyridin-4-yl]-(5-methyl-pyridin-2-yl)-amine; and
[2-Methyl-7-(5-methyl-pyridin-3-yl)-thiazolo[4,5-c]pyridin-4-yl]-(2-methyl-thiazol-4-yl)-amine.

Preferred compounds of formula I are further those, wherein R³ is phenyl substituted by halogen or by —S(O)₂-lower alkyl and R² is methyl-substituted thiazolyl or is methyl-substituted pyrimidinyl, for example the following compounds:
[7-(3,5-Difluoro-phenyl)-2-methyl-thiazolo[4,5-c]pyridin-4-yl]-(2-methyl-thiazol-4-yl)-amine;
[7-(3-Methanesulfonyl-phenyl)-2-methyl-thiazolo[4,5-c]pyridin-4-yl]-(4-methyl-thiazol-2-yl)-amine;
[7-(3-Methanesulfonyl-phenyl)-2-methyl-thiazolo[4,5-c]pyridin-4-yl]-(2-methyl-pyrimidin-4-yl)-amine;
[7-(3-Methanesulfonyl-phenyl)-2-methyl-thiazolo[4,5-c]pyridin-4-yl]-(2-methyl-thiazol-4-yl)-amine; and
[7-(3,5-Difluoro-phenyl)-2-methyl-thiazolo[4,5-c]pyridin-4-yl]-(4-methyl-thiazol-2-yl)-amine.

Preferred compounds of formula I are further those, wherein R³ is pyrimidinyl and R² is methyl-substituted thiazolyl, methyl-substituted pyridinyl or methyl-substituted pyrimidinyl, for example the following compounds:
(2-Methyl-7-pyrimidin-5-yl-thiazolo[4,5-c]pyridin-4-yl)-(4-methyl-thiazol-2-yl)-amine
Methyl-pyrimidin-4-yl)-(2-methyl-7-pyrimidin-5-yl-thiazolo[4,5-c]pyridin-4-yl)-amine;
Methyl-pyridin-4-yl)-(2-methyl-7-pyrimidin-5-yl-thiazolo[4,5-c]pyridin-4-yl)-amine; and
(2-Methyl-7-pyrimidin-5-yl-thiazolo[4,5-c]pyridin-4-yl)-(2-methyl-thiazol-4-yl)-amine.

Preferred compounds of formula I are further those, wherein R³ is pyridin-4-yl substituted by halogen or lower alkyl and R² is methyl-substituted thiazolyl or methyl-substituted pyridinyl, for example the following compounds:
[7-(2-Chloro-pyridin-4-yl)-2-methyl-thiazolo[4,5-c]pyridin-4-yl]-(2-methyl-pyridin-4-yl)-amine;
[7-(2-Chloro-pyridin-4-yl)-2-methyl-thiazolo[4,5-c]pyridin-4-yl]-(2-methyl-thiazol-4-yl)-amine; and
[2-Methyl-7-(2-methyl-pyridin-4-yl)-thiazolo[4,5-c]pyridin-4-yl]-(2-methyl-thiazol-4-yl)-amine.

Preferred compounds of formula I are further those, wherein R³ is oxazolyl substituted by lower alkyl and R² is methyl-substituted thiazolyl, for example the following compound:
[7-(3,5-Dimethyl-isoxazol-4-yl)-2-methyl-thiazolo[4,5-c]pyridin-4-yl]-(2-methyl-thiazol-4-yl)-amine.

The compounds of formula I of the invention can be prepared according to various processes.

In an embodiment, the process of the invention comprises the following variants a) reacting a compound of formula II:

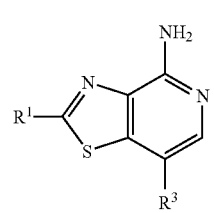

with a compound of formula

R²X to obtain a compound of formula I:

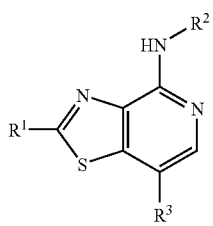

wherein X is chlorine, bromine or iodine, preferably bromine and $R^1$, $R^2$ and $R^3$ are as defined above, and if desired, converting the compounds obtained into pharmaceutically acceptable acid addition salts, or b) reacting a compound of formula III:

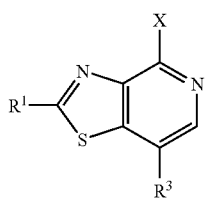

with a compound of formula $NH_2R^2$ to obtain a compound of formula I

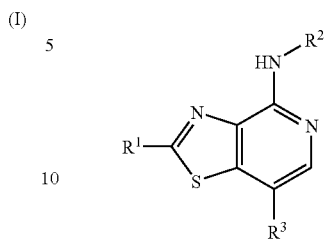

wherein $R^1$, $R^2$ and $R^3$ are as defined above and X is chlorine, bromine or iodine, preferably chlorine, and if desired, converting the compounds obtained into pharmaceutically acceptable acid addition salts.

In accordance with step a), the desired compound of formula I can be prepared as follows: A compound of formula II and a compound of formula $R^2Br$ are dissolved in dry dioxane. 4,5-Bis(diphenylphosphino)-9,9-dimethylxanthene, cesium carbonate and tri(dibenzylideneacetone)dipalladium chloroform complex are added, and the reaction mixture is stirred for about 20 hrs at 130° C. to obtain a compound of formula I.

The various processes of the invention are described in more detail in the following schemes 1 and 2 and in examples 1-23. All starting materials (e.g. compound IV) are known compounds, which can be either prepared according to known methods from commercially available products or are directly commercially available.

Scheme 1

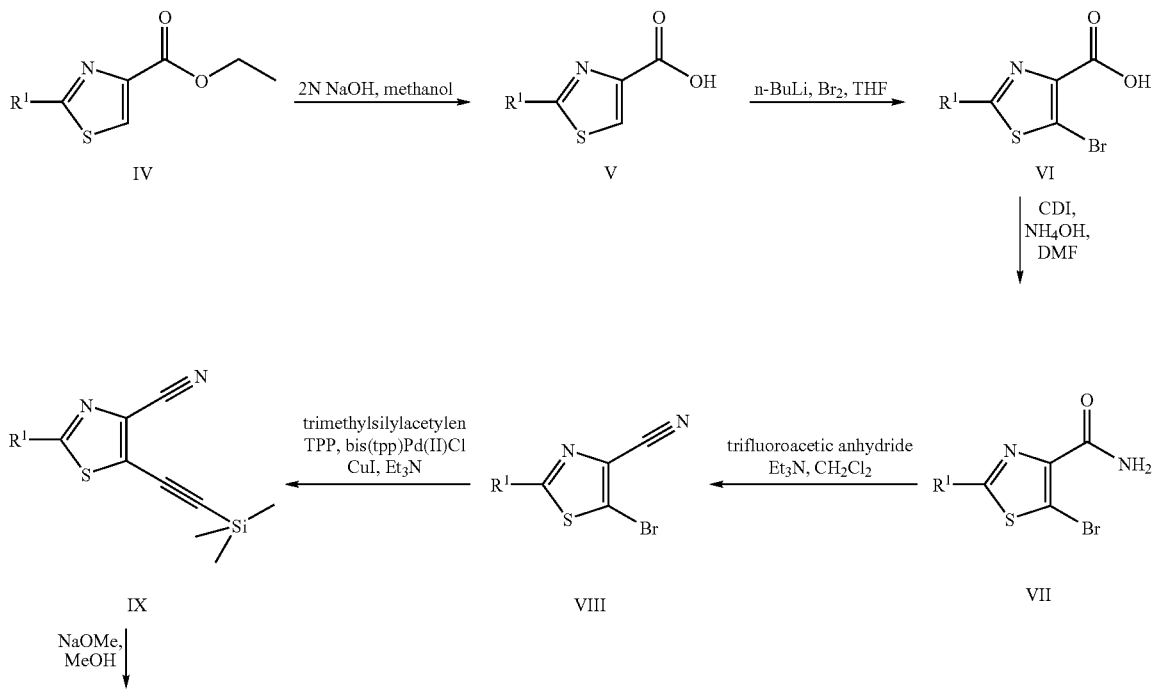

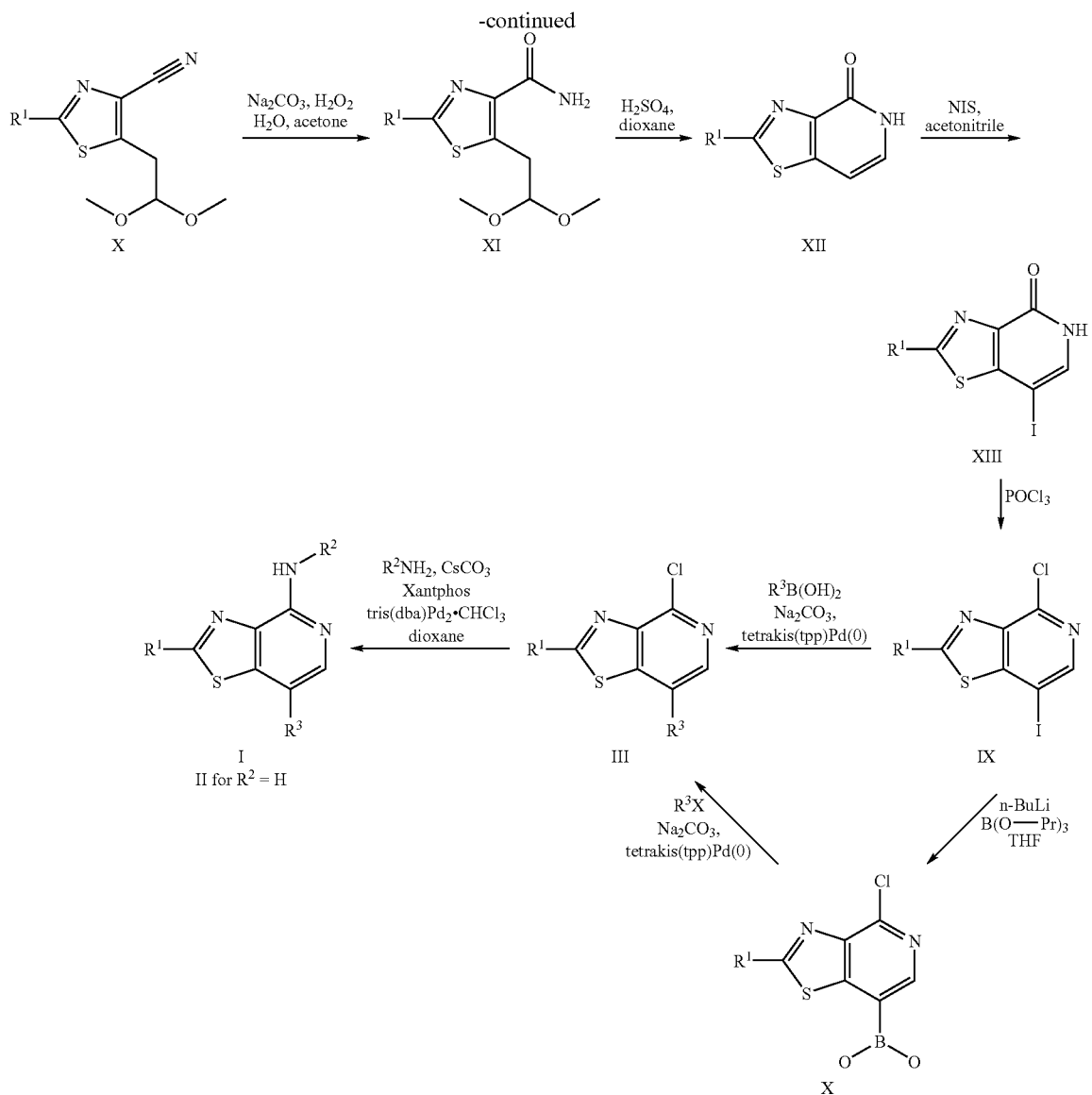

wherein the substituents $R^1$, $R^2$ and $R^3$ are as described above and wherein $R^3$ is other than hydrogen.

Scheme 2

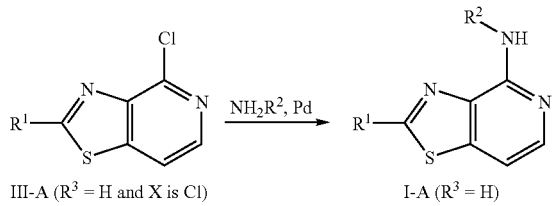

wherein the substituents $R^1$ and $R^2$ are as described above.

Compounds of formula III-A (compounds of formula III wherein $R^3$ is H and X is Cl) can be prepared in accordance with the description in scheme 1 or according to WO2002/044189 starting from commercially available products. Then, a compound of formula III-A and a compound of formula $NH_2R^2$ are dissolved in dry dioxane. 4,5-bis(diphenylphosphino)-9,9-dimethylxanthene, cesium carbonate and tri(dibenzylideneacetone)dipalladium chloroform complex are added, and the reaction mixture is stirred under microwave irradiation for 50 minutes at about 150° C. The reaction mixture is then evaporated and purified in conventional manner.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute or chronic pain, urinary incontinence, liver damage or failure whether drug or disease induced, obesity or Fragile-X or autism, acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression and drug dependency as shown in references such as "*European Journal of Pharmacology* (2004), 497(1), 25-27."; "*Journal of Hepatology* (2003), 38(2), 179-187"; and "*Hepatology (Philadelphia)* (2000), 31(3), 649-655".

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method: For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronised in 15 mM Tris-HCl, 120 mM NaCl, 100 mM KCl, 25 mM CaCl$_2$, 25 mM MgCl$_2$ binding buffer at pH 7.4 to a final assay concentration of 20 µg protein/well.

Saturation isotherms were determined by addition of twelve [$^3$H]MPEP concentrations (0.04-100 nM) to these membranes (in a total volume of 200 µL) for 1 h at 4° C. Competition experiments were performed with a fixed concentration of [$^3$H]MPEP (2 nM) and IC$_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 µM MPEP. The radioactivity on the filter was counted (3 min) on a Packard Top-count microplate scintillation counter with quenching correction after addition of 45 µl of microscint 40 (Canberra Packard S.A., Zürich, Switzerland) and shaking for 20 min.

For functional assays, [Ca$^{2+}$]i measurements were performed as described previously by Porter et al. [Br. J. Pharmacol. 128:13-20 (1999)] on recombinant human mGlu 5a receptors in HEK-293 cells. The cells were dye loaded using Fluo 4-AM (obtainable by FLUKA, 0.2 µM final concentration). [Ca$^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving IC$_{50}$, and Hill coefficient using iterative non linear curve fitting software (Xcel fit).

For binding experiments the Ki values of the compounds tested are given. The Ki value is defined by the following formula:

$$K_i = IC_{50}/[1+L/K_d]$$

in which the IC$_{50}$ values are those concentrations of the compounds tested which cause 50% inhibition of the competing radioligand ([$^3$H]MPEP). L is the concentration of radioligand used in the binding experiment and the K$_d$ value of the radioligand is empirically determined for each batch of membranes prepared.

The compounds of the present invention are mGluR 5a receptor antagonists. The activities of the compounds of formulae I, Ia and Ib as measured in the assay described above and as presented in the table hereafter are in the range of K$_i$ < 400 nM.

| Example | Ki (nM) |
| --- | --- |
| 1 | 26 |
| 2 | 37 |
| 3 | 42 |
| 4 | 40 |
| 5 | 167 |
| 9 | 61 |
| 14 | 45 |
| 17 | 128 |
| 19 | 29 |
| 20 | 87 |

The present invention also provides pharmaceutical compositions containing compounds of formula I or their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts and the like can be used, for example, as such as carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I, I-a, or I-b and/or pharmaceutically acceptable acid addition salts thereof and, if desired, one or more other therapeutically valuable substances into a galenical administration form together with one or more therapeutically inert carriers.

The compounds of formula I are metabotropic glutamate receptor antagonists. Compounds of formula I are distinguished by having valuable therapeutic properties. They can be used in the treatment or prevention of mGluR5 receptor mediated disorders.

Such disorders are acute and/or chronic neurological disorders, in particular acute or chronic pain, urinary incontinence, gastrointestinal reflux disorder, liver damage or failure whether drug or disease induced, obesity or Fragile-X or autism, acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression and drug dependency.

The invention provides a method for treating such acute and/or chronic neurological disorders. In particular, the invention provides a method for treating Alzheimer's disease which comprises administering to an individual a therapeutically effective amount of a compound of formula I or a pharmaceutically acceptable salt thereof. The invention also provides a method for treating senile dementia which comprises administering to an individual a therapeutically effective amount of a compound of formula I or a pharmaceutically acceptable salt thereof. The invention also provides a method for treating Parkinson's disease which comprises administering to an individual a therapeutically effective amount of a compound of formula I or a pharmaceutically acceptable salt thereof. The invention also provides a method for treating acute or chronic pain which comprises administering to an individual a therapeutically effective amount of a compound of formula I or a pharmaceutically acceptable salt thereof.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention:

EXAMPLE 1

Chloro-phenyl)-(2-methyl-thiazolo[4,5-c]pyridin-4-yl)-amine

4-Chloro-2-methyl-thiazolo[4,5-c]pyridine (100 mg, 0.54 mmol) (Example A) and 3-chloroaniline (90 mg, 0.70 mmol) were dissolved in 3 ml dry dioxane. 4,5-bis(diphenylphosphino)-9,9-dimethylxanthene (63 mg, 0.1 mmol), cesium carbonate (350 mg, 1.08 mmol) and tri(dibenzylideneacetone)dipalladium chloroform complex (56 mg, 0.05 mmol) were added and the reaction mixture was stirred for 16 hrs at 120° C. The reaction mixture was then evaporated and purified by flash chromatography on silica gel (heptane/ethyl acetate 90:10->30:70 gradient). The desired product was obtained as a yellow solid (20 mg, 13%), MS: m/e=276.3 (M+H$^+$).

EXAMPLE 2

(2-Methyl-7-pyridin-3-yl-thiazolo[4,5-c]pyridin-4-yl)-(2-methyl-thiazol-4-yl)-amine Step 1: 4-Chloro-2-methyl-7-pyridin-3-yl-thiazolo[4,5-c]pyridine Tetrakis(triphenylphosphine)palladium(0) (52 mg, 0.05 mmol) was dissolved in 8 ml toluene. 4-Chloro-7-iodo-2-methyl-thiazolo[4,5-c]pyridine (280 mg, 0.90 mmol) (Example B), 3-pyridineboronic acid (133 mg, 1.08 mmol), 2M sodium carbonate (2.70 ml, 5.4 mmol) and 2 ml ethanol were added and the mixture stirred at 80° C. for 6 hrs. The reaction mixture was extracted with water and two times ethyl acetate. The organic extracts were washed with water and brine, dried with sodium sulfate, filtered and evaporated. The crude product was purified by flash chromatography on silica gel (heptane/ethyl acetate 9:1->0:100 gradient). The desired compound was obtained as a light yellow solid (100 mg, 42%), MS: m/e=263.1 (M+H$^+$).

Step 2: (2-Methyl-7-pyridin-3-yl-thiazolo[4,5-c]pyridin-4-yl)-(2-methyl-thiazol-4-yl)-amine 4-Chloro-2-methyl-7-pyridin-3-yl-thiazolo[4,5-c]pyridine (100 mg, 0.38 mmol) and 4-amino-2-methylthiazole (44 mg, 0.38 mmol) (Example C) were dissolved in 3 ml dry dioxane. 4,5-bis(diphenylphosphino)-9,9-dimethylxanthene (44 mg, 0.08 mmol) and cesium carbonate (200 mg, 0.61 mmol) were added and this mixture was evacuated and back-filled with argon several times to remove oxygen from the solution. Tris(dibenzylideneacetone)dipalladium chloroform complex (38 mg, 0.035 mmol) was added and the reaction mixture was stirred for 1 hour at 100° C. The reaction mixture was then evaporated and purified by flash chromatography on silica gel (heptane/ethyl acetate 90:10->0:100 gradient) and recrystallization in diisopropylether. The desired product was obtained as a yellow solid (20 mg, 15%), MS: m/e 354.1 (M+H$^+$).

EXAMPLE 3

(2-Methyl-7-pyridin-3-yl-thiazolo[4,5-c]pyridin-4-yl)-(4-methyl-thiazol-2-yl)-amine The title compound, MS: m/e=340.1 (M+H$^+$), was prepared in accordance with the general method of example 2, step 2 from 4-chloro-2-methyl-7-pyridin-3-yl-thiazolo[4,5-c]pyridine and 2-amino-4-methylthiazole.

EXAMPLE 4

Fluoro-pyridin-2-yl)-(2-methyl-7-pyridin-3-yl-thiazolo[4,5-c]pyridin-4-yl)-amine The title compound, MS: m/e=338.1 (M+H$^+$), was prepared in accordance with the general method of example 2, step 2 from 4-chloro-2-methyl-7-pyridin-3-yl-thiazolo[4,5-c]pyridine and 2-amino-5-fluoropyridine.

EXAMPLE 5

Methyl-1H-pyrazol-3-yl)-(2-methyl-7-pyridin-3-yl-thiazolo[4,5-c]pyridin-4-yl)-amine The title compound, MS: m/e=323.3 (M+H$^+$), was prepared in accordance with the general method of example 2, step 2 from 4-chloro-2-methyl-7-pyridin-3-yl-thiazolo[4,5-c]pyridine and 3-amino-1-methylpyrazole.

EXAMPLE 6

[7-(3,5-Difluoro-phenyl)-2-methyl-thiazolo[4,5-c]pyridin-4-yl]-(2-methyl-thiazol-4-yl)-amine The title compound, MS: m/e=375.1 (M+H$^+$), was prepared in accordance with the general method of example 2, step 1 and step 2 from 4-chloro-7-iodo-2-methyl-thiazolo[4,5-c]pyridine (Example B), 3,5-difluorophenylboronic acid and 4-amino-2-methylthiazole (Example C).

EXAMPLE 7

[7-(5-Fluoro-pyridin-3-yl)-2-methyl-thiazolo[4,5-c]pyridin-4-yl]-(4-methyl-thiazol-2-yl)-amine The title compound, MS: m/e=358.2 (M+H$^+$), was prepared in accordance with the general method of example 2, step 1 and step 2 from 4-chloro-7-iodo-2-methyl-thiazolo[4,5-c]pyridine (Example B), 3-fluoro-5-pyridineboronic acid and 2-amino-4-methylthiazole.

EXAMPLE 8

[7-(5-Fluoro-pyridin-3-yl)-2-methyl-thiazolo[4,5-c]pyridin-4-yl]-(2-methyl-pyrimidin-4-yl)-amine The title compound, MS: m/e=353.2 (M+H$^+$), was prepared in accordance with the general method of example 2, step 1 and step 2 from 4-chloro-7-iodo-2-methyl-thiazolo[4,5-c]pyridine (Example B), 3-fluoro-5-pyridineboronic acid and 4-amino-2-methylpyrimidine.

EXAMPLE 9

Methyl-7-pyrimidin-5-yl-thiazolo[4,5-c]pyridin-4-yl)-(4-methyl-thiazol-2-yl)-amine The title compound, MS: m/e=341.1 (M+H$^+$), was prepared in accordance with the general method of example 2, step 1 and step 2 from 4-chloro-7-iodo-2-methyl-thiazolo[4,5-c]pyridine (Example B), 5-pyrimidineboronic acid and 2-amino-4-methylthiazole.

EXAMPLE 10

Methyl-pyrimidin-4-yl)-(2-methyl-7-pyrimidin-5-yl-thiazolo[4,5-c]pyridin-4-yl)-amine The title compound, MS: m/e=336.2 (M+H$^+$), was prepared in accordance with the general method of example 2, step 1 and step 2 from 4-chloro-7-iodo-2-methyl-thiazolo[4,5-c]pyridine (Example B), 5-pyrimidineboronic acid and 4-amino-2-methylpyrimidine.

EXAMPLE 11

(2-Methyl-pyridin-4-yl)-(2-methyl-7-pyrimidin-5-yl-thiazolo[4,5-c]pyridin-4-yl)-amine The title compound, MS: m/e=335.2 (M+H$^+$), was prepared in accordance with the general method of example 2, step 1 and step 2 from 4-chloro-7-iodo-2-methyl-thiazolo[4,5-c]pyridine (Example B), 5-pyrimidineboronic acid and 2-methyl-4-aminopyridine.

EXAMPLE 12

(2-Methyl-7-pyrimidin-5-yl-thiazolo[4,5-c]pyridin-4-yl)-(2-methyl-thiazol-4-yl)-amine The title compound, MS: m/e=341.0 (M+H$^+$), was prepared in accordance with the general method of example 2, step 1 and step 2 from 4-chloro-7-iodo-2-methyl-thiazolo[4,5-c]pyridine (Example B), 5-pyrimidineboronic acid and 4-amino-2-methylthiazole (Example C).

EXAMPLE 13

[7-(2-Chloro-pyridin-4-yl)-2-methyl-thiazolo[4,5-c]pyridin-4-yl]-(2-methyl-pyridin-4-yl)-amine The title compound, MS: m/e=368.1 (M+H$^+$), was prepared in accordance with the general method of example 2, step 1 and step 2 from 4-chloro-7-iodo-2-methyl-thiazolo[4,5-c]pyridine (Example B), 2-chloropyridin-4-boronic acid and 2-methyl-4-aminopyridine.

EXAMPLE 14

[7-(2-Chloro-pyridin-4-yl)-2-methyl-thiazolo[4,5-c]pyridin-4-yl]-(2-methyl-thiazol-4-yl)-amine The title compound, MS: m/e=374.0 (M+H$^+$), was prepared in accordance with the general method of example 2, step 1 and step 2 from 4-chloro-7-iodo-2-methyl-thiazolo[4,5-c]pyridine (Example B), 2-chloropyridin-4-boronic acid and 4-amino-2-methylthiazole (Example C).

EXAMPLE 15

[7-(5-Fluoro-pyridin-3-yl)-2-methyl-thiazolo[4,5-c]pyridin-4-yl]-(2-methyl-thiazol-4-yl)-amine The title compound, MS: m/e=358.2 (M+H$^+$), was prepared in accordance with the general method of example 2, step 1 and step 2 from 4-chloro-7-iodo-2-methyl-thiazolo[4,5-c]pyridine (Example B), 3-fluoro-5-pyridineboronic acid and 4-amino-2-methylthiazole (Example C).

EXAMPLE 16

[7-(3-Methanesulfonyl-phenyl)-2-methyl-thiazolo[4,5-c]pyridin-4-yl]-(4-methyl-thiazol-2-yl)-amine The title compound, MS: m/e=417.2 (M+H$^+$), was prepared in accordance with the general method of example 2, step 1 and step 2 from 4-chloro-7-iodo-2-methyl-thiazolo[4,5-c]pyridine (Example B), (3-methylsulfonylphenyl)boronic acid and 2-amino-4-methylthiazole.

EXAMPLE 17

[7-(3-Methanesulfonyl-phenyl)-2-methyl-thiazolo[4,5-c]pyridin-4-yl]-(2-methyl-pyrimidin-4-yl)-amine The title compound, MS: m/e=412.3 (M+H$^+$), was prepared in accordance with the general method of example 2, step 1 and step 2 from 4-chloro-7-iodo-2-methyl-thiazolo[4, 5-c]pyridine (Example B), (3-methylsulfonylphenyl)boronic acid and 4-amino-2-methylpyrimidine.

EXAMPLE 18

[7-(3-Methanesulfonyl-phenyl)-2-methyl-thiazolo[4,5-c]pyridin-4-yl]-(2-methyl-thiazol-4-yl)-amine The title compound, MS: m/e=417.2 (M+H$^+$), was prepared in accordance with the general method of example 2, step 1 and step 2 from 4-chloro-7-iodo-2-methyl-thiazolo[4,5-c]pyridine (Example B), (3-methylsulfonylphenyl)boronic acid and 4-amino-2-methylthiazole (Example C).

EXAMPLE 19

[7-(3,5-Difluoro-phenyl)-2-methyl-thiazolo[4,5-c]pyridin-4-yl]-(4-methyl-thiazol-2-yl)-amine The title compound, MS: m/e=375.1 (M+H$^+$), was prepared in accordance with the general method of example 2, step 1 and step 2 from 4-chloro-7-iodo-2-methyl-thiazolo[4,5-c]pyridine (Example B), 3,5-difluorophenylboronic acid and 2-amino-4-methylthiazole.

EXAMPLE 20

[7-(5-Fluoro-pyridin-3-yl)-2-methyl-thiazolo[4,5-c]pyridin-4-yl]-(5-methyl-pyridin-2-yl)-amine The title compound, MS: m/e=352.2 (M+H$^+$), was prepared in accordance with the general method of example 2, step 1 and step 2 from 4-chloro-7-iodo-2-methyl-thiazolo[4,5-c]pyridine (Example B), 3-fluoro-5-pyridineboronic acid and 2-amino-5-methylpyridine.

EXAMPLE 21

[2-Methyl-7-(5-methyl-pyridin-3-yl)-thiazolo[4,5-c]pyridin-4-yl]-(2-methyl-thiazol-4-yl)-amine The title compound, MS: m/e=354.3 (M+H$^+$), was prepared in accordance with the general method of example 2, step 1 and step 2 from 4-chloro-2-methyl-thiazolo[4,5-c]pyridine-7-boronic acid (Example D), 3-bromo-5-methylpyridine and 4-amino-2-methylthiazole (Example C).

EXAMPLE 22

[2-Methyl-7-(2-methyl-pyridin-4-yl)-thiazolo[4,5-c]pyridin-4-yl]-(2-methyl-thiazol-4-yl)-amine The title compound, MS: m/e=354.1 (M+H$^+$), was prepared in accordance with the general method of example 2, step 1 and step 2 from 4-chloro-2-methyl-thiazolo[4,5-c]pyridine-7-boronic acid (Example D), 4-bromo-2-methylpyridine and 4-amino-2-methylthiazole (Example C).

EXAMPLE 23

[7-(3,5-Dimethyl-isoxazol-4-yl)-2-methyl-thiazolo[4,5-c]pyridin-4-yl]-(2-methyl-thiazol-4-yl)-amine The title compound, MS: m/e=358.1 (M+H$^+$), was prepared in accordance with the general method of example 2, step 1 and step 2 from 4-chloro-7-iodo-2-methyl-thiazolo[4,5-c]pyridine (Example B), 3,5-dimethylisoxazole-4-boronic acid and 4-amino-2-methylthiazole (Example C).

Synthesis of Intermediates

EXAMPLE A

4-Chloro-2-methyl-thiazolo[4,5-c]pyridine

Step 1: 3-Nitro-pyridin-4-ol
4-Methoxy-3-nitropyridine (25.0 g, 162 mmol) in 220 ml conc. hydrobromic acid (48%) was refluxed at 100° C. for 16 hrs. The reaction mixture was cooled, poured into ice water and neutralized with 155 ml conc. NaOH (32%). The suspension was stirred for 10 min. at 5° C. and filtered. The solid was washed with water and dried at 50° C. and <30 mbar for 1 hour. The desired product was obtained as a light yellow solid (20.2 g, 89%).

Step 2: 3-Amino-pyridin-4-ol
3-Nitro-pyridin-4-ol (20.0 g, 143 mmol) was suspended in 1000 ml methanol and 20 ml DMF. Palladium on charcoal (2.0 g, 10% Pd) was added and the mixture was hydrogenated at ambient temperature for 4 hrs. The suspension was filtered and the solvent was evaporated. The desired product was obtained as a pink oil (26 g, quantitative).

Step 3: N-(4-Hydroxy-pyridin-3-yl)-acetamide
3-Amino-pyridin-4-ol (15.0, 136 mmol) was suspended in 200 ml dichloromethane and N-ethyldiisopropylamine (82 ml, 477 mmol) was added. A solution of acetylchloride (10.6 ml, 150 mmol) in 150 ml dichloromethane was added dropwise at ambient temperature. The reaction mixture was stirred at reflux for 3 hrs and evaporated to dryness. The residue was stirred in methanol and filtered. The solvent was evaporated and the desired product was obtained as a white solid (7.2 g, 35%), MS: m/e=151.1 (M+H$^+$).

Step 4: 2-Methyl-thiazolo[4,5-c]pyridine
N-(4-Hydroxy-pyridin-3-yl)-acetamide (3.0 g, 19.7 mmol) was dissolved in 150 ml pyridine and phosphor pentasulfide (4.4 g, 19.7 mmol) was added. The reaction mixture was stirred at reflux for 2 hrs and evaporated to dryness. The residue was dissolved in water and the pH was adjusted to 8 with saturated sodium bicarbonate-solution. The aqueous layer was extracted two times with ethyl acetate. The organic extracts were dried with sodium sulfate, filtered and evaporated. The crude product (2.3 g, 78%) was used without any further purification for the next step.

Step 5: 2-Methyl-thiazolo[4,5-c]pyridine 5-oxide
2-Methyl-thiazolo[4,5-c]pyridine (2.3 g, 15.3 mmol) was dissolved in 150 ml chloroform and 3-chloroperoxybenzoic acid (4.15 g, 16.8 mmol) was added. The reaction mixture was stirred at ambient temperature for 1 hour and then evaporated. The residue was purified by flash chromatography on silica gel (dichloromethane/methanol 100:0->90:10 gradient). The desired product was obtained as a white solid (2.1 g, 83%), MS: m/e=167.2 (M+H$^+$).

Step 6: 4-Chloro-2-methyl-thiazolo[4,5-c]pyridine
2-Methyl-thiazolo[4,5-c]pyridine 5-oxide (230 mg, 1.38 mmol) was refluxed 2 hrs in 4 ml of phosphoryl chloride. The reaction mixture was evaporated and extracted with ethyl acetate and saturated sodium bicarbonate-solution. The organic extracts were dried with sodium sulfate, filtered and evaporated. The residue was purified by flash chromatography on silica gel (heptane/ethyl acetate 90:10->0:100 gradient). The desired product was obtained as a light yellow solid (180 mg, 70%), MS: m/e=185.1 (M+H+).

EXAMPLE B

4-Chloro-7-iodo-2-methyl-thiazolo[4,5-c]pyridine

Step 1: 2-Methyl-thiazole-4-carboxylic acid

Ethyl 2-methylthiazole-4-carboxylate (17.0 g, 99.3 mmol) was dissolved in 150 ml of methanol and 2N NaOH (150 ml, 300 mmol) was added. The reaction mixture was stirred for 2 hours at room temperature. Methanol was evaporated and the residue was acidified with 2N HCl to pH 2. The aqueous layer was extracted two times with ethyl acetate. The organic extracts were dried with sodium sulfate, filtered and evaporated. The crude product (13.0 g, 91%) was used without any further purification for the next step.

Step 2: 5-Bromo-2-methyl-thiazole-4-carboxylic acid

2-Methyl-thiazole-4-carboxylic acid (13.0 g, 90.8 mmol) was dissolved in 750 ml THF and cooled to −75° C. n-BuLi (1.6M in THF; 120 ml, 190.7 mmol) was added dropwise in 30 minutes. The red suspension was stirred for 15 min. at −75° C. and 30 min. at 0° C. A solution of bromine (5.1 ml, 100 mmol) in 20 ml cyclohexane was added dropwise at −75° C. and stirring was continued at room temperature for 2 hrs. The reaction mixture was quenched with 20 ml water, evaporated and acidified with 2N HCl to pH 2. The aqueous layer was extracted two times with ethyl acetate. The combined organic extracts were dried with sodium sulfate, filtered and evaporated. The crude product (16.4 g, 81%) [MS: m/e=223.0 (M+H+)] was used without any further purification for the next step.

Step 3: 5-Bromo-2-methyl-thiazole-4-carboxylic acid amide

5-Bromo-2-methyl-thiazole-4-carboxylic acid (14.4 g, 64.8 mmol) was dissolved in 100 ml DMF and CDI (11.6 g, 71.3 mmol) was added. The solution was stirred for 2 hrs at 60° C., cooled and NH4OH (150 ml, 973 mmol) was added. The reaction mixture was stirred over night at room temperature and extracted two times with ethyl acetate and water. The organic extracts were washed four times with water, dried with sodium sulfate, filtered and evaporated. The crude product (11.3 g, 79%) [MS: m/e=222.8 (M+H+)] was used without any further purification for the next step.

Step 4: 5-Bromo-2-methyl-thiazole-4-carbonitrile

5-Bromo-2-methyl-thiazole-4-carboxylic acid amide (11.3 g, 51.1 mmol) was dissolved in 150 ml dichloromethane and triethylamine (14.2 ml, 102.2 mmol) was added. Trifluoroaceticanhydride (14.3 ml, 102.2 mmol) was added dropwise at 0° C. and the mixture stirred without cooling for 2 hrs. The reaction mixture was quenched with saturated NaHCO3-solution and extracted with ethyl acetate. The organic extract was washed with brine, dried with sodium sulfate, filtered and evaporated. The crude product was purified by flash chromatography on silica gel (heptane/ethyl acetate 90:10->20:80 gradient). The desired compound was obtained as a light yellow solid (6.4 g, 62%), MS: m/e=204.0 (M+H+).

Step 5: 2-Methyl-5-trimethylsilanylethynyl-thiazole-4-carbonitrile

5-Bromo-2-methyl-thiazole-4-carbonitrile (4.8 g, 23.6 mmol) was suspended in 50 ml triethyl amine. Trimethylsilylacetylene (4.64 g, 47.3 mmol), triphenylphosphine (186 mg, 0.7 mmol) and bis(triphenylphosphine)palladium(II) chloride (0.83 g, 1.18 mmol) were added and this mixture was evacuated and purged with argon several times to remove oxygen from the solution. Copper(I)iodide (45 mg, 0.24 mmol) was added and the reaction mixture was stirred at 70° C. for 5 hrs. The residue was taken up in water, extracted three times with ethyl acetate and several times with water. The combined organic extracts were dried with sodium sulfate, filtered and evaporated. The crude product was purified by chromatography on silica gel (heptane/ethyl acetate 90:10-> 1:1 gradient). The desired product was obtained as a black solid (4.1 g, 79%).

Step 6: 5-(2,2-Dimethoxy-ethyl)-2-methyl-thiazole-4-carbonitrile

2-Methyl-5-trimethylsilanylethynyl-thiazole-4-carbonitrile (4.56 g, 20.7 mmol) was dissolved in 45 ml methanol and sodium methoxide (5.4N in methanol, 11.5 ml, 62 mmol) was added. The reaction mixture was stirred for 2 hrs at reflux and extracted two times with ethyl acetate and saturated NaHCO3-solution. The organic extracts were dried with sodium sulfate, filtered and evaporated. The crude product (4.5 g, >100%) was used without any further purification for the next step.

Step 7: 5-(2,2-Dimethoxy-ethyl)-2-methyl-thiazole-4-carboxylic acid amide

2M Na2CO3-solution (64 ml, 127 mmol), H2O2 (30%, 43.3 ml, 424 mmol) and 45 ml water were placed and a solution of 5-(2,2-dimethoxy-ethyl)-2-methyl-thiazole-4-carbonitrile (4.5 g, 21 mmol) in 45 ml acetone was added dropwise at room temperature. The white suspension was stirred for 2 hrs. Acetone was evaporated and the aqueous residue was extracted three times with ethyl acetate. The organic extracts were dried with sodium sulfate, filtered and evaporated. The crude product (4.8 g, 98%) was used without any further purification for the next step.

Step 8: 2-Methyl-5H-thiazolo[4,5-c]pyridin-4-one 5-(2,2-Dimethoxy-ethyl)-2-methyl-thiazole-4-carboxylic acid amide (1.0 g, 4.3 mmol) was dissolved in 35 ml dioxane and 0.3 ml conc. sulfuric acid was added. The reaction mixture was stirred for 2 hrs at room temperature. The white suspension was cooled to 0° C. and stirred for 10 min. The suspension was filtered and washed with cold dioxane. The solid was dried for 1 hour at 50° C. and <30 mbar. The desired product was obtained as a white solid (0.7 g, 97%), MS: m/e=167.1 (M+H+).

Step 9: 7-Iodo-2-methyl-5H-thiazolo[4,5-c]pyridin-4-one

2-Methyl-5H-thiazolo[4,5-c]pyridin-4-one (770 mg, 4.6 mmol) was suspended in 25 ml acetonitrile and N-iodosuccinimide (1.04 g, 4.6 mmol) was added. The reaction mixture was refluxed for 3 hrs. The brown suspension was cooled to 5° C. and stirred for 15 min. The solid was filtered, washed with cold acetonitrile and dried for 1 hour at 50° C. and <30 mbar. The crude product (830 mg, 61%) [MS: m/e=292.9 (M+H+)] was used without any further purification for the next step.

Step 10: 4-Chloro-7-iodo-2-methyl-thiazolo[4,5-c]pyridine

7-Iodo-2-methyl-5H-thiazolo[4,5-c]pyridin-4-one (880 mg, 3.01 mmol) was suspended in POCl3 (8.25 ml, 90.4 mmol) and refluxed for 4 hrs. The black reaction mixture was evaporated and poured as a dichloromethane solution in ice water. The aqueous layer was neutralized with solid NaHCO3 to pH 7 and extracted three times with dichloromethane. The combined organic extracts were dried with magnesium sulfate, filtered and evaporated. The crude product was purified by chromatography on silica gel (dichloromethane/methanol 100:0->95:5 gradient). The desired product was obtained as a light yellow solid (280 mg, 30%), MS: m/e=311.0 (M+H+).

EXAMPLE C

4-Amino-2-methylthiazole

The title compound can be prepared in accordance with the preparation described in patent EP 321115.

EXAMPLE D

4-Chloro-2-methyl-thiazolo[4,5-c]pyridine-7-boronic acid

4-Chloro-7-iodo-2-methyl-thiazolo[4,5-c]pyridine (Example B) (2.35 g, 7.56 mmol) and triisopropylborate (1.8 ml, 7.94 mmol) were dissolved in 70 ml THF and cooled to −75° C. n-Butyllithium (1.6M in hexane) (5.0 ml, 7.94 mmol) was added drop wise at −70° C. The reaction mixture was stirred for 1 hour at −75° C. and for 1 hour without ice-bath. 10 ml 2N HCl-solution were added and extracted three times with ethyl acetate. The organic layers were washed with brine, dried over $Na_2SO_4$ and concentrated in vacuo. The residue was crystallized in acetonitrile to get the desired compound as a red solid (520 mg, 30%), MS: m/e=229.2 (M+H$^+$).

Preparation of the Pharmaceutical Compositions

EXAMPLE I

Tablets of the following composition are produced in a conventional manner:

|  | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE II

Tablets of the following composition are produced in a conventional manner:

|  | mg/Tablet |
| --- | --- |
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE III

Capsules of the following composition are produced:

|  | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of formula I:

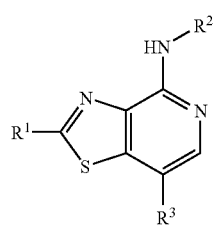

(I)

wherein
  $R^1$ is hydrogen, halogen, cyano, lower alkoxy, lower alkyl, lower alkyl substituted by halogen, cycloalkyl, —(CH$_2$)$_n$—O-lower alkyl, or —C(O)R' wherein R' is lower alkyl, lower alkoxy or N(R)$_2$;
  $R^2$ is aryl or 5- or 6-membered heteroaryl;
  $R^3$ is hydrogen, OR, N(R)$_2$, lower alkyl, cycloalkyl, aryl, heterocycloalkyl, 5- or 6-membered heteroaryl, lower alkyl substituted by halogen, or —C(O)R' wherein R' is lower alkyl, lower alkoxy or N(R)$_2$;
    wherein the aryl, cycloalkyl, heterocycloalkyl or 5-or 6-membered heteroaryl groups for $R^2$ and $R^3$ are unsusbtituted or substituted by halogen, cyano, lower alkyl, lower alkoxy, S(O)$_2$-alkyl, S(O)-alkyl, or —C(O)R' wherein R' is lower alkyl, lower alkoxy or N(R)$_2$;
  R is hydrogen or lower alkyl;
  n is 0, 1 or 2;
  or a pharmaceutically acceptable salt thereof.

2. The compound of claim 1

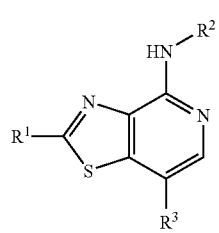

(I)

wherein
R¹ is lower alkyl;
R² is phenyl, thiazolyl, pyridinyl, pyrimidinyl or pyrazolyl, wherein the rings are unsubstituted or substituted by halogen or lower alkyl;
R³ is hydrogen, phenyl, pyridinyl, pyrimidinyl or isoxazolyl which each are unsubstituted or substituted by halo or —SO₂-lower alkyl.

3. The compound of claim 1

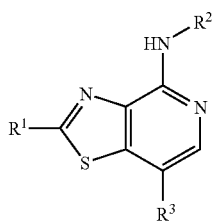

(I)

wherein
R¹ is lower alkyl;
R² is phenyl, thiazolyl, pyridinyl or pyrazolyl, wherein the rings are unsubstituted or substituted by halogen or lower alkyl;
R³ is hydrogen or pyridinyl;
or a pharmaceutically acceptable salt thereof.

4. The compound of claim 1, wherein R¹ is methyl.

5. The compound of claim 1, wherein R³ is hydrogen and R² is phenyl substituted by halogen.

6. The compound of claim 5, which compound is (3-chloro-phenyl)-(2-methyl-thiazolo[4,5-c]pyridin-4-yl)-amine.

7. The compound of claim 1, wherein R³ is pyridinyl-3-yl.

8. The compound of claim 7, wherein R³ is pyridin-3-yl and R² is methyl-substituted thiazolyl.

9. The compound of claim 8, selected from the group consisting of (2-methyl-7-pyridin-3-yl-thiazolo[4,5-c]pyridin-4-yl)-(2-methyl-thiazol-4-yl)-amine and (2-methyl-7-pyridin-3-yl-thiazolo[4,5-c]pyridin-4-yl)-(4-methyl-thiazol-2-yl)-amine.

10. The compound of claim 7, wherein R³ is pyridin-3-yl and R² is halogen-substituted pyridinyl.

11. The compound of claim 10, which compound is (5-fluoro-pyridin-2-yl)-(2-methyl-7-pyridin-3-yl-thiazolo[4,5-c]pyridin-4-yl)-amine.

12. The compound of claim 7, wherein R³ is pyridin-3-yl and R² is methyl substituted pyrazol-3-yl.

13. The compound of claim 12, which compound is (1-methyl-1H-pyrazol-3-yl)-(2-methyl-7-pyridin-3-yl-thiazolo[4,5-c]pyridin-4-yl)-amine.

14. The compound of claim 1, wherein R³ is phenyl substituted by halogen or by —S(O)₂-lower alkyl and R² is methyl-substituted thiazolyl or is methyl-substituted pyrimidinyl.

15. The compound of claim 14, selected from the group consisting of:
[7-(3,5-Difluoro-phenyl)-2-methyl-thiazolo[4,5-c]pyridin-4-yl]-(2-methyl-thiazol-4-yl)-amine;
[7-(3-Methanesulfonyl-phenyl)-2-methyl-thiazolo[4,5-c]pyridin-4-yl]-(4-methyl-thiazol-2-yl)-amine;
[7-(3-Methanesulfonyl-phenyl)-2-methyl-thiazolo[4,5-c]pyridin-4-yl]-(2-methyl-pyrimidin-4-yl)-amine;
[7-(3-Methanesulfonyl-phenyl)-2-methyl-thiazolo[4,5-c]pyridin-4-yl]-(2-methyl-thiazol-4-yl)-amine; and
[7-(3,5-Difluoro-phenyl)-2-methyl-thiazolo[4,5-c]pyridin-4-yl]-(4-methyl-thiazol-2-yl)-amine.

16. The compound of claim 1, wherein R³ is pyridin-3-yl substituted by halogen or lower alkyl and R² is methyl-substituted thiazolyl, methyl-substituted pyridinyl or methyl-substituted pyrimidinyl.

17. The compound of claim 16, selected from the group consisting of:
[7-(5-Fluoro-pyridin-3-yl)-2-methyl-thiazolo[4,5-c]pyridin-4-yl]-(4-methyl-thiazol-2-yl)-amine;
[7-(5-Fluoro-pyridin-3-yl)-2-methyl-thiazolo[4,5-c]pyridin-4-yl]-(2-methyl-pyrimidin-4-yl)-amine;
[7-(5-Fluoro-pyridin-3-yl)-2-methyl-thiazolo[4,5-c]pyridin-4-yl]-(2-methyl-thiazol-4-yl)-amine;
[7-(5-Fluoro-pyridin-3-yl)-2-methyl-thiazolo[4,5-c]pyridin-4-yl]-(5-methyl-pyridin-2-yl)-amine; and
[2-Methyl-7-(5-methyl-pyridin-3-yl)-thiazolo[4,5-c]pyridin-4-yl]-(2-methyl-thiazol-4-yl)-amine.

18. The compound of claim 1, wherein R³ is pyrimidinyl and R² is methyl-substituted thiazolyl, methyl-substituted pyridinyl or methyl-substituted pyrimidinyl.

19. The compound of claim 18, selected from the group consisting of:
(2-Methyl-7-pyrimidin-5-yl-thiazolo[4,5-c]pyridin-4-yl)-(4-methyl-thiazol-2-yl)-amine
(2-Methyl-pyridin-4-yl)-(2-methyl-7-pyrimidin-5-yl-thiazolo[4,5-c]pyridin-4-yl)-amine;
(2-Methyl-pyridin-4-yl)-(2-methyl-7-pyrimidin-5-yl-thiazolo[4,5-c]pyridin-4-yl)-amine; and
(2-Methyl-7-pyrimidin-5-yl-thiazolo[4,5-c]pyridin-4-yl)-(2-methyl-thiazol-4-yl)-amine.

20. The compound of claim 1, wherein R³ is pyridin-4-yl substituted by halogen or lower alkyl and R² is methyl-substituted thiazolyl or methyl-substituted pyridinyl.

21. The compound of claim 20, selected from the group consisting of:
[7-(2-Chloro-pyridin-4-yl)-2-methyl-thiazolo[4,5-c]pyridin-4-yl]-(2-methyl-pyridin-4-yl)-amine;
[7-(2-Chloro-pyridin-4-yl)-2-methyl-thiazolo[4,5-c]pyridin-4-yl]-(2-methyl-thiazol-4-yl)-amine; and
[2-Methyl-7-(2-methyl-pyridin-4-yl)-thiazolo[4,5-c]pyridin-4-yl]-(2-methyl-thiazol-4-yl)-amine.

22. The compound of claim 1, wherein R³ is oxazolyl substituted by lower alkyl and R² is methyl-substituted thiazolyl.

23. The compound of formula I according to claim 22, which compound is:
[7-(3,5-Dimethyl-isoxazol-4-yl)-2-methyl-thiazolo[4,5-c]pyridin-4-yl]-(2-methyl-thiazol-4-yl)-amine.

24. A pharmaceutical composition comprising a therapeutically effective amount of a compound of formula I

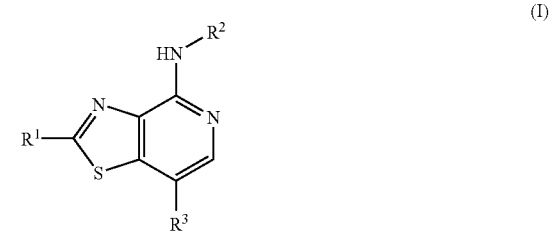

(I)

wherein
R¹ is hydrogen, halogen, cyano, lower alkoxy, lower alkyl, lower alkyl substituted by halogen, cycloalkyl, —$(CH_2)_n$—O-lower alkyl, or —C(O)R' wherein R' is lower alkyl, lower alkoxy or $N(R)_2$;

$R^2$ is aryl or 5- or 6-membered heteroaryl;

$R^3$ is hydrogen, OR, $N(R)_2$, lower alkyl, cycloalkyl, aryl, heterocycloalkyl, 5- or 6-membered heteroaryl, lower alkyl substituted by halogen, or —C(O)R' wherein R' is lower alkyl, lower alkoxy or $N(R)_2$;

wherein the aryl, cycloalkyl, heterocycloalkyl or 5- or 6-membered heteroaryl groups for $R^2$ and $R^3$ are unsusbtituted or substituted by halogen, cyano, lower alkyl, lower alkoxy, $S(O)_2$-alkyl, S(O)-alkyl, or —C(O)R' wherein R' is lower alkyl, lower alkoxy or $N(R)_2$;

R is hydrogen or lower alkyl;

n is 0,1 or 2;

or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 7,659,401 B2 Page 1 of 1
APPLICATION NO. : 11/590087
DATED : February 9, 2010
INVENTOR(S) : Jaeschke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 367 days.

Signed and Sealed this

Twenty-eighth Day of December, 2010

David J. Kappos
*Director of the United States Patent and Trademark Office*